United States Patent [19]
Ellinger et al.

[11] Patent Number: 5,265,460
[45] Date of Patent: Nov. 30, 1993

[54] DENSITY DETERMINATION OF AIRCRAFT FUEL BASED ON THE SENSED TEMPERATURE VELOCITY OF SOUND, AND DIELECTRIC CONSTANT OF THE FUEL

[75] Inventors: S. Michael Ellinger, Charlotte; Bruce R. Kline, Starksboro, both of Vt.

[73] Assignee: Simmonds Precision Products, Inc., Akron, Ohio

[21] Appl. No.: 682,605

[22] Filed: Apr. 9, 1991

[51] Int. Cl.[5] .............................. G01N 9/00
[52] U.S. Cl. .................................... 73/32 R
[58] Field of Search ............ 73/32 A, 32 R; 364/577, 364/558

[56] References Cited

U.S. PATENT DOCUMENTS

| | | |
|---|---|---|
| 3,478,589 | 11/1969 | Birken .................. 73/32 R |
| 4,011,746 | 3/1977 | Weitz, Jr. et al. ............ 73/32 R |
| 4,232,544 | 11/1980 | Stansfeld ............... 73/32 A |
| 4,354,377 | 10/1982 | Stansfeld ............... 73/32 A |
| 4,442,700 | 4/1984 | Swoboda ............... 73/32 A |
| 4,466,272 | 8/1984 | Stansfeld ............... 73/32 A |
| 4,739,494 | 4/1988 | Torii ..................... 364/558 |
| 4,815,323 | 3/1989 | Ellinger et al. ............ 73/32 A |
| 4,959,228 | 9/1990 | Skrgatic et al. ........... 73/32 A |

Primary Examiner—Hezron E. Williams
Assistant Examiner—Nashmiya Ashraf
Attorney, Agent, or Firm—David M. Ronyak; Stephen J. Schultz

[57] ABSTRACT

Method and apparatus for determining jet fuel density. A microprocessor monitors the temperature, velocity of sound and dielectric constant of a jet fuel. The microprocessor determines the type of jet fuel and the density of the fuel using data from jet fuel samples of a known density and a least-squares-fit of the test data.

10 Claims, 2 Drawing Sheets

DENSITY DETERMINATION OF AIRCRAFT FUEL BASED ON THE SENSED TEMPERATURE VELOCITY OF SOUND, AND DIELECTRIC CONSTANT OF THE FUEL

FIELD OF THE INVENTION

The present invention concerns method and apparatus for sensing a characteristic of a fluid and more specifically, concerns method and apparatus for determining the density of jet fuel or alternately, the type of jet fuel.

BACKGROUND ART

Aircraft fuel measuring systems are required to measure mass which is a product of density and volume. Prior art mechanisms for monitoring fuel density have included vibrating spools, hydrometer floats and inference based systems using dielectric constant or speed of sound.

U.S. Pat. No. 4,232,544 which issued to James W. Stansfeld and is assigned to Solartron Electronic Group, Limited discloses apparatus for sensing the density of a fluid. Similar structures are disclosed in U.S. Pat. Nos. 4,354,377 to Stansfeld and 4,466,272 to Stansfeld. Each of these prior art patents discloses an elongated tube and an electrical transducer for exciting the elongated tube at its natural frequency of vibration. Changes of the density of a fluid contacting the tube modify the frequency of vibration. By correlating this change in frequency with a change in density, it is possible for such structures to determine the density of a fluid. Systems embodying a vibrating tube sensing device such as those disclosed in these patents can produce accurate results, but are expensive. Additionally, the size of such systems can make them inappropriate for certain applications.

Another category of prior art densitometers are commercially available from Simmonds Precision Aircraft Systems, Division of B. F. Goodrich Aerospace, assignee of the present invention. One such system uses an ultrasonic gauging technique which senses the speed at which sound passes through the fluid and the temperature of the fluid to determine a density as disclosed in U.S. Pat. No. 4,815,323 to Ellinger et al.

It is also known in the prior art to determine fuel density by measuring the dielectric constant of the fuel using a capacitance measuring technique. These systems infer a density based upon the measured dielectric constant of the fuel. While these systems are less costly to implement than the densitometer using a vibrating tube, they are also somewhat less accurate.

DISCLOSURE OF THE INVENTION

The present invention concerns method and apparatus for determining jet fuel density. Furthermore, the invention provides a mechanism to discriminate between different types of jet fuel.

In accordance with one embodiment of the invention, apparatus for determining the density of a fluid includes one or more probes immersible within the fluid for measuring the temperature, velocity of sound, and dielectric constant of the fluid. Signals corresponding to these measurements are routed from the one or more probes to a computer which computes a density of the fuel. The density determination is based upon data from sample fuel having a known density.

In a preferred embodiment of the invention, the probes are mounted within a jet aircraft fuel tank and signals corresponding to the temperature, velocity of sound and dielectric constant are routed to a computer which generates an output signal corresponding to the density. This signal is routed away from the computer and used in computing fuel mass.

In accordance with a preferred technique for programming the computer, as the temperature of a sample fuel is varied across a specified range, the density, velocity of sound, and dielectric constant of the aircraft fuel are monitored. A least-squares-fit calculation is performed to derive a functional relationship between the three independent variables of temperature, velocity of sound and dielectric constant and the dependent variable of fuel density. This relationship is then programmed into the computer so that as signals corresponding to temperature, velocity of sound and dielectric constant are routed to the computer, a fuel density output is generated.

Various least-squares-fit approximation methods can be utilized to improve the accuracy of the disclosed density calculation. The resultant approximation using the three parameters of velocity of sound, dielectric constant and temperature yields a more accurate determination than any one or two of the parameters taken alone or combined. This produces an accurate density determination that is lower cost than the vibrating tube calculation technique and more accurate than prior art techniques relying upon either dielectric constant or velocity of sound alone.

One advantage of this present invention is a reduced cost, yet accurate, densitometer. Other objects, advantages, and features of the invention will become understood by reviewing the best mode for practicing the invention which is described in conjunction with the accompanying drawings.

BEST MODE FOR PRACTICING THE INVENTION

Figure 1:
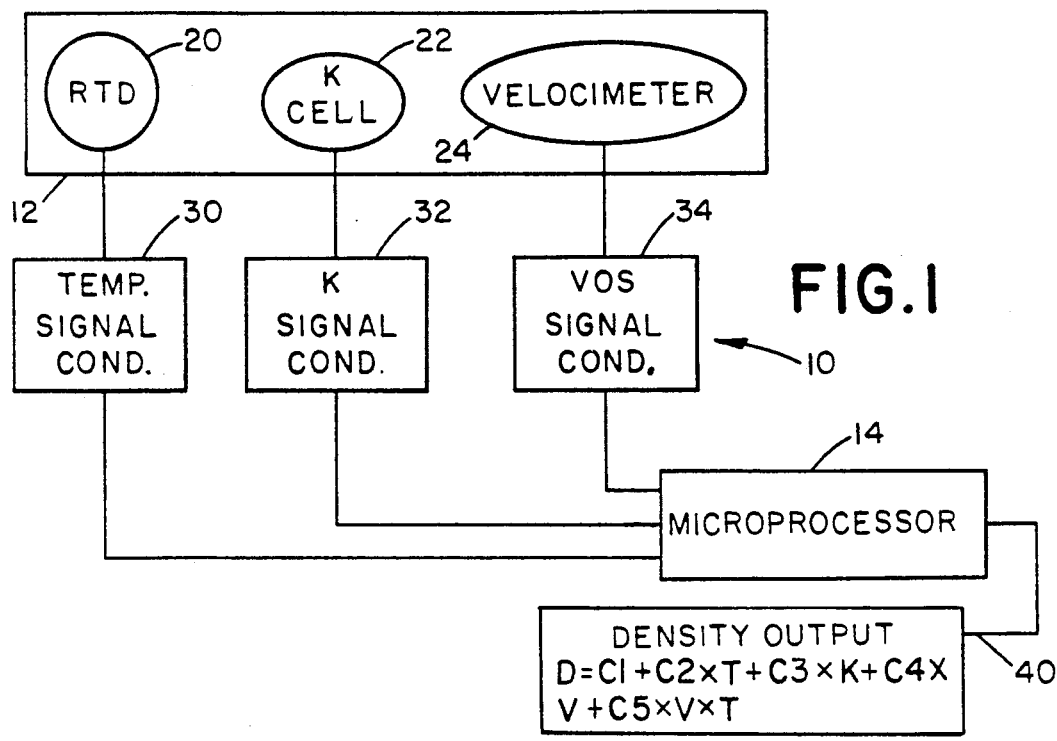
FIG. 1 is a schematic showing a system for monitoring the density of jet fuel.

FIG. 1 schematically discloses a monitoring system 10 for determining the density of a fluid contained within a container 12. A microprocessor controller 14 performs density calculations based upon sensed characteristics of the fluid within the container. A preferred use of the invention is in conjunction with a system for monitoring the density of jet fuel. The density determination is then used for computing the mass of jet fuel. In this embodiment, the container 12 therefore constitutes a fuel tank containing jet fuel of either type A or type B.

Commercially available probes or sensors 20, 22, 24 are immersed within jet fuel contained within the fuel tank 12 and provide signals corresponding to the temperature, dielectric constant and velocity of sound within the jet fuel.

The sensor 20 for determining temperature utilizes a platinum RTD having a well-defined relation between resistance and temperature. By applying a signal across the RTD and monitoring the current passing through the RTD in response to the applied signal, it is possible to obtain an output directly related to the temperature of the RTD. One suitable RTD based probe 20 for use in conjunction with the system 10 is available commercially under the designation PR-14-2-100-1/4-6-E and is available from Omega.

The dielectric probe 22 contains a capacitive circuit wherein parallel-spaced plates are energized by a control signal. By monitoring the capacitance across the plates, it is possible to determine the dielectric constant of the material between the plates. In this way, the dielectric constant of the jet fuel contained within the fuel tank 12 can be determined. A suitable probe 22 for providing an output related to the dielectric constant of the fuel is commercially available under the designation P/N 387003 from Simmond Precision.

The third probe 24 monitors the velocity of sound within the jet fuel. This probe utilizes an ultrasonic transducer activated by a signal having a specified frequency. Signals are transmitted from the transducer and return signals monitored. The time between activation of the transducer and return of the reflected signal gives an indication of the speed of sound within the jet fuel. A suitable probe 24 for monitoring the speed of sound within a fluid is commercially available under the designation Model 6080 from Nusonics.

The three probes 20, 22, 24 generate output signals that are transmitted to three signal conditioning circuits 30, 32, 34. These signal conditioning circuits filter out extraneous signals which may be generated in the region of the probes 20, 22, 24. The signal conditioning circuits are tailored for the particular signal being monitored. Commercially available circuits for accomplishing this signal conditioning are known in the prior art and are available from Omega, Andeen-Itagerling, and Nusonics respectively.

Each of the signal conditioning circuits 30, 32, 34 generates a corresponding output which is transmitted to the microprocessor 14. In a preferred embodiment of the invention, the microprocessor comprises an 8-bit microprocessor having an input/output port whose pins are periodically monitored by a control algorithm executed within the microprocessor. The control algorithm acquires the data from the signal conditioning circuits and temporarily stores that data in preparation for a density determination.

The probes 20, 22, 24 and signal conditioning circuits 30, 32, 34 generate output signals that are accurate to within one degree Celsius for the probe 20, to within 0.5% of the dielectric constant for the probe 22, and to within 0.3% of the velocity from the probe 24.

The microprocessor 14 contains a stored control algorithm for periodically acquiring data from the probes 20, 22, 24 and determining the density of the jet fuel. The density calculation is based upon previously acquired data utilizing sample jet fuels. In accordance with the preferred embodiment of the present invention, fuel samples having known densities are tested and a database of test data evaluated. A least-squares-fit is applied to the sample data and incorporated into the control algorithm of the microprocessor 40.

The preferred density determination technique utilizes an equation of the form:

$$D = C1 + C2 \times T + C3 \times K + C4 \times V + C5 \times V \times T \quad (1)$$

Each of the constants C1–C5 is derived from the test data taken on known fuel samples and programmed into the control algorithm of the microprocessor. In a preferred embodiment of the invention, these constants are stored in E²ROM memory either in the microprocessor or in a memory circuit coupled to the microprocessor 14. The constants C1–C5 vary depending upon the particular fuel under examination. Stated another way, if the microprocessor is sensing type A jet fuel constants C1–C5 would be used to calculate jet fuel density, but if jet fuel type B is sensed, different constants C1'–C5', for example, are used.

The form of the density determination equation is first order in T, K and V with one product term $V \times T$. In general, the least-squares-fit approach can be applied to a theoretical curve that includes other products of the V, T and K variables such as the products of KV and KVT.

Figure 2:
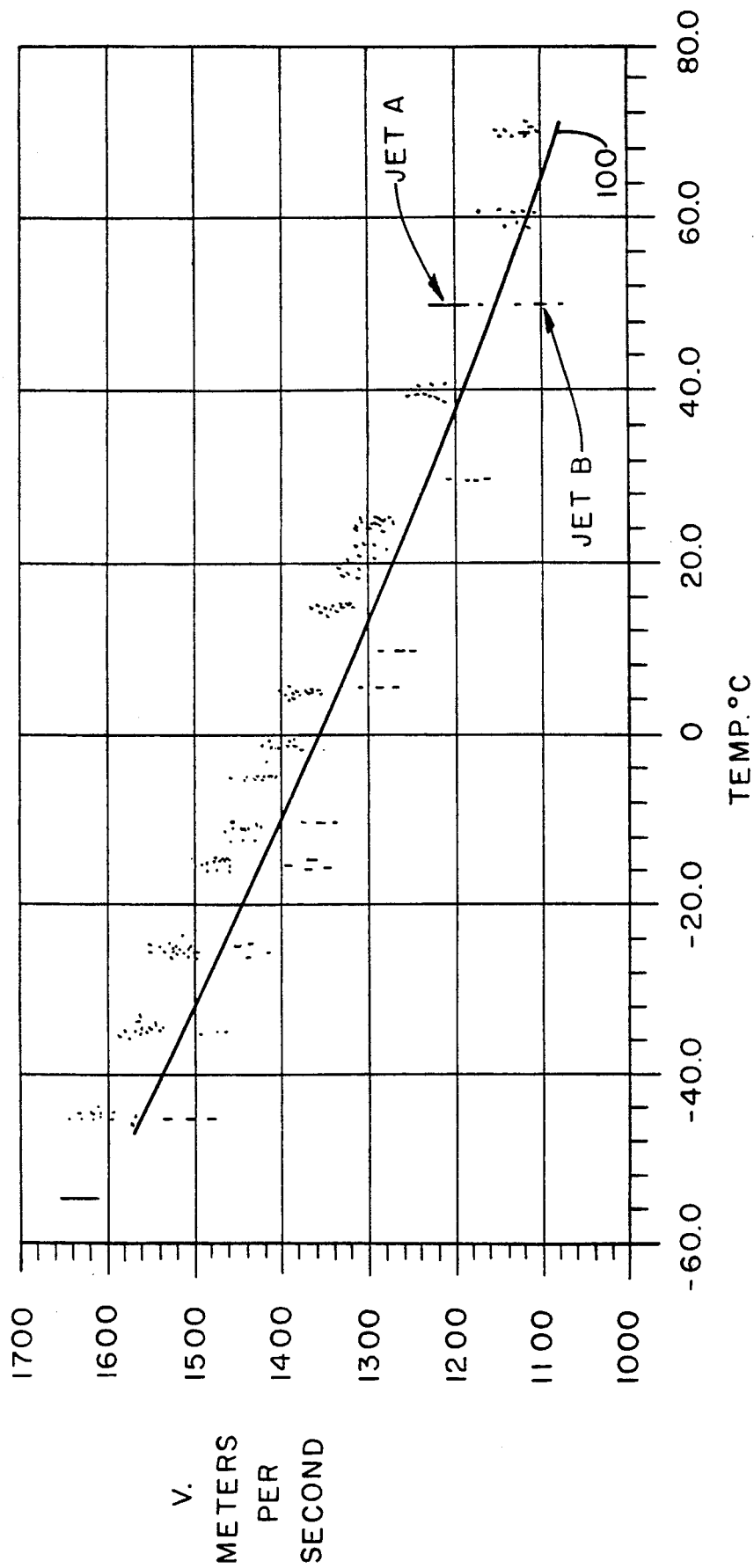
FIG. 2 is a graph showing velocity of sound as a function of temperature for two different types of jet fuel.

Before performing the density calculation, the microprocessor 14 must determine the type of jet fuel that is being monitored. FIG. 2 graphically depicts the variation with temperature in the speed of sound for type A and B jet fuel. A mean between the two measurements defines a boundary 100 for determining which of the two types of jet fuel is being sensed. The microprocessor 14 uses the speed of sound and temperature measurement to determine the fuel type. If, for a given sensed temperature the sensed velocity falls below the boundary 100, the measurement is for type B fuel and one set of constants C1'–C5' is used in Equation 1. If the sensed velocity is above the boundary 100, the fuel is type A and a second set of constants C1–C5 is used in Equation 1.

The equation for the boundary 100 is also derived from a least-squares-fit using sample fuel. An equation of the form $V = K1 + K2T + K3T^2$ is derived for type A and type B jet fuel and a mean value for the constants K1–K3 determined. This equation is stored in the microprocessor control program and used to determine the type of jet fuel and hence the correct set of constants C1–C5.

In accordance with the preferred embodiment of the invention, the microprocessor 40 includes a separate output port for transmitting a density signal 40 from the microprocessor 40 to other control systems within an airplane. Specifically, an 8-bit signal is routed from the microprocessor using either a serial or a parallel communications protocol to a separate computer for computing jet fuel mass. This allows the system 10 to be contained in a self-contained unit having common well-known interfacing with other control systems within the aircraft.

In an alternate design, the microprocessor may be replaced by a central computer within the aircraft which monitors signals corresponding to the temperature, velocity of sound and dielectric constant. This computer would receive these signals either through special dedicated communications paths or along a bus using bus contention techniques well-known in the art. In this alternate design, the computer not only determines the density based upon input signals taken from the communications bus, but would also use these density calculations in computing fuel mass.

Figure 3:
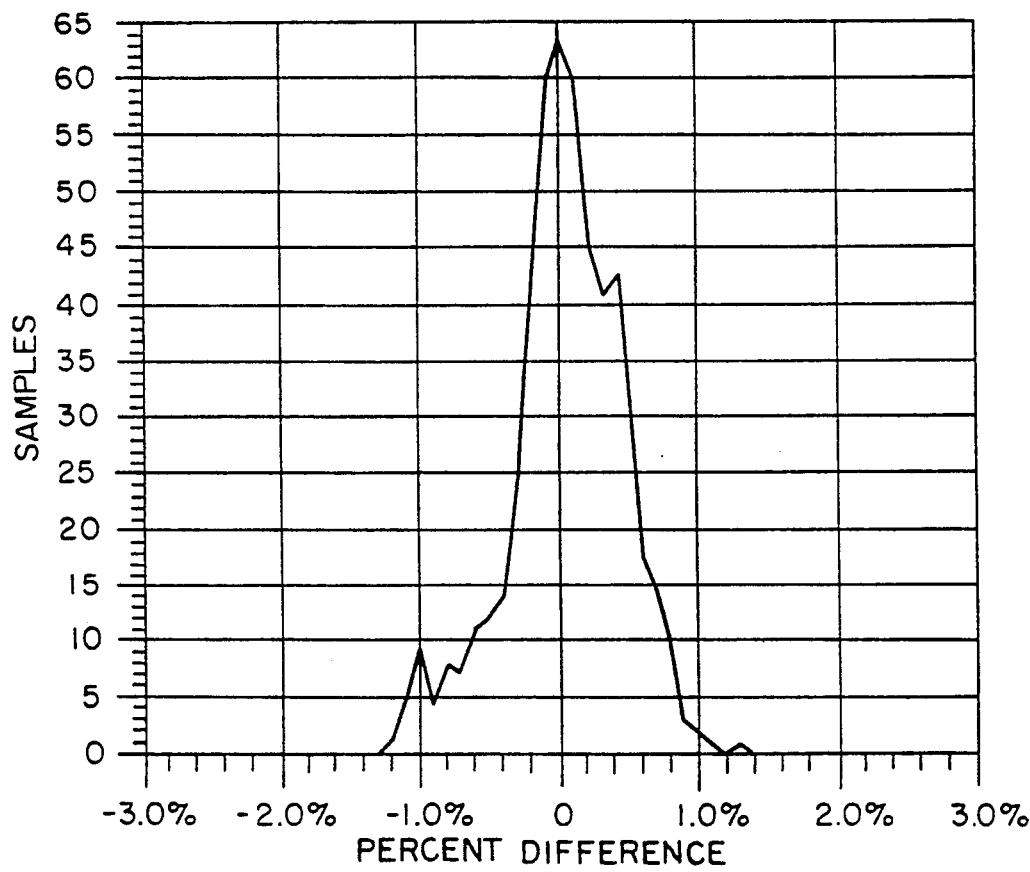
FIG. 3 is a histogram showing results of fuel density measurements using the method and apparatus of the present invention.

FIG. 3 is a histogram showing the accuracy of measurements performed using the preferred embodiment of the invention. The graph plots percent difference between the calculated density (from Equation 1) and sensed density for 85 samples. Each parameter (including density) was measured at seven temperatures from −55° C. to +70° C. The measurements of temperature, velocity of sound and dielectric constant were then used to derive the constants C1–C5 of Equation 1. The FIG. 3 histogram has an standard error of 0.405%.

It is appreciated that a preferred embodiment of the present invention has been described and it is the intent that the invention include all modifications or alterations from the disclosed preferred design falling within the spirit or scope of the appended claims.

We claim:

1. Apparatus for determining the density of aircraft fuel comprising:
   a) a sensor including a first probe immersible within an aircraft fuel for measuring the temperature of the aircraft fuel; a second probe immersible within the aircraft fuel for measuring the velocity of sound in the aircraft fuel; and a third probe immersible within the aircraft fuel for measuring a dielectric constant of the aircraft fuel;
   b) a controller for computing a density of the aircraft fuel based upon a combination of the temperature sensed by the first probe, the velocity of sound sensed by the second probe, and dielectric constant of the aircraft fuel sensed by the third probe; and
   c) an interface for routing signals corresponding to the temperature, velocity of sound, and dielectric constant from the probes of said sensor to the controller;
   d) said controller comprising a programmable controller for determining the density aircraft fuel of unknown density based on known density data from a plurality of aircraft fuel samples whose density has been previously determined and whose density variations as a function of temperature, velocity of sound, and dielectric constant are stored in a memory and used by the controller to compute the density of the aircraft fuel whose density is unknown.

2. The apparatus of claim 1 wherein the programmable controller comprises an output port for outputing a signal related to the computed density.

3. The apparatus of claim 1 wherein the programmable controller comprises circuitry for determining a type of fuel from the velocity of sound and sensed temperature.

4. The apparatus of claim 3 wherein the programmable controller determines the density by evaluating an expression of the form:

$$C1+C2\times T+C3\times K+C4\times V+C5\times T\times V$$

where T is sensed temperature, K is sielectric constant, V is velocity of sound and C1, C2, C3, C4 and C5 are constants which depend on the type of fuel whose density is computed.

5. A method for determining aircraft fuel density comprising the steps of:
   a) measuring a temperature, density, velocity of sound, and dielectric constant for a plurality of test fuel samples;
   b) measuring the temperature, velocity of sound, and dielectric constant of a fuel of unknown density;
   c) determining a functional relation between a combination of temperature, dielectric constant, velocity of sound, and aircraft fuel density based upon measurements of the plurality of test fuel samples;
   d) determining the density of fuel of unknown density by calculating its density from the functional relation relating the temperature, velocity of sound and dielectric constant to aircraft fuel density obtained from the test fuel samples.

6. Apparatus for determining the density of aircraft fuel comprising:
   a) a sensor immersible within an aircraft fuel including probes for sensing the temperature, velocity of sound, and dielectric constant of an aircraft fuel;
   b) a microprocessor for computing a density of the aircraft fuel based upon a combination of the sensed temperature, velocity of sound, and dielectric constant of aircraft fuel whose density is unknown; and
   c) an interface for routing signals from the sensor corresponding to said temperature, velocity of sound, and dielectric constant to the microprocessor;
   d) said microprocessor including a control program for determining the density of the aircraft fuel based on density data from aircraft fuel test samples whose density as a function of temperature, velocity of sound, and dielectric constant is stored in a memory of the microprocessor and used to compute the density from sensed temperature, velocity of sound and dielectric constant of the aircraft fuel whose density is unknown.

7. The apparatus of claim 6 wherein the microprocessor comprises means for outputing a signal related to the computed density of the aircraft fuel.

8. The apparatus of claim 6 wherein the microprocessor comprises means for determining a type of fuel from the velocity of sound and sensed temperature.

9. The apparatus of claim 8 wherein the microprocessor determines the density by evaluating an expression of the form:

$$C1+C2\times T+C3\times K+C4\times V+C5\times T\times V$$

where T is sensed temperature, K is dielectric constant, V is velocity of sound and C1, C2, C3, C4, and C5 are constants which depend on the type of fuel whose density is computed.

10. Apparatus for determining the density of an aircraft fuel comprising:
   a) a sensor including three probes immersible within an aircraft fuel for sensing the temperature, velocity of sound, and dielectric constant of the aircraft fuel;
   b) a controller for computing a density of the aircraft fuel based upon a combination of the sensed temperature, sensed velocity of sound, and sensed dielectric constant of the aircraft fuel; and
   c) an interface for routing signals from the three probes corresponding to the sensed temperature, velocity of sound, and dielectric constant of the controller;
   d) said controller comprising circuitry for determining the density of the aircraft fuel based on density data from aircraft fuel samples whose density variations with temperature, velocity of sound, and dielectric constant have been previously determined and stored in said circuitry for use in computing a density of the aircraft fuel whose density is unknown.

* * * * *